United States Patent [19]

Brown et al.

[11] Patent Number: 5,200,417
[45] Date of Patent: Apr. 6, 1993

[54] SUBSTITUTED 4-AMINO-ISOQUINOLINE COMPOUNDS, PHARMACEUTICAL COMPOSITION AND METHOD OF USE

[75] Inventors: Thomas H. Brown; Robert J. Ife; Colin A. Leach, all of Welwyn, England

[73] Assignee: Smithkline Beecham Intercredit B.V., Welwyn Garden, England

[21] Appl. No.: 504,781

[22] Filed: Apr. 4, 1990

[30] Foreign Application Priority Data

Apr. 12, 1989 [GB] United Kingdom ............... 8908229

[51] Int. Cl.$^5$ ................... A61K 31/47; C07D 217/22
[52] U.S. Cl. ................... 514/310; 546/143
[58] Field of Search ................... 546/143; 514/310

[56] References Cited

U.S. PATENT DOCUMENTS

| | | | |
|---|---|---|---|
| 2,666,059 | 1/1954 | Davis et al. | 546/143 |
| 3,644,366 | 2/1972 | Jeanmart et al. | 546/143 |
| 3,702,849 | 11/1972 | Cronin et al. | 546/143 |
| 3,748,333 | 7/1973 | Jeanmart et al. | 546/143 |

OTHER PUBLICATIONS

Gittos, et al., "Chemical Abstracts", vol. 72, 1970, Col. 12601w.
Omar, "Chemical Abstracts", vol. 78, 1973, Col. 15992j.
Hazzaa, et al., "Chemical Abstracts", vol. 79, 1973, Col. 53150m.
Roushdi, et al. (I), "Chemical Abstracts", vol. 80, 1974, Col. 59838j.
Roushdi, et al. (II), "Chemical Abstracts", vol. 80, 1974, Col. 59839j.
Omar, et al., "Chemical Abstracts", vol. 81, 1974, Col. 12741c.
Jeanmart, et al., "Chemical Abstracts", vol. 22, 1969, Col. 72:111309p.
J. Pharm. Soc. Japan, 1961, 77, 90.

Primary Examiner—C. Warren Ivy
Assistant Examiner—James H. Turnipseed
Attorney, Agent, or Firm—Linda E. Hall; Stuart R. Suter; Edward T. Lentz

[57] ABSTRACT

Isoquinoline compounds, compositions containing them and their use in the inhibition of gastric acid secretion in mammals. A compound of the invention is 1-[(2-Methoxyphenylmethyl)amino]isoquinoline hydrochloride.

9 Claims, No Drawings

SUBSTITUTED 4-AMINO-ISOQUINOLINE COMPOUNDS, PHARMACEUTICAL COMPOSITION AND METHOD OF USE

The present invention relates to novel substituted isoquinoline derivatives, processes for their preparation, intermediates useful in their preparation, pharmaceutical compositions containing them and their use in therapy.

Accordingly, the present invention provides, in a first aspect, a compound of structure (I):

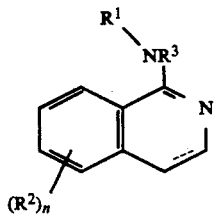

(I)

in which $R^1$ is $C_{1-6}$alkyl, $C_{3-6}$cycloalkyl, $C_{3-6}$cycloalkyl$C_{1-6}$alkyl, phenyl$(CH_2)_m$ the phenyl group being optionally substituted by 1-3 radicals selected from $C_{1-6}$alkyl, $C_{1-6}$alkoxy, amino $C_{1-6}$alkylthio, halogen, cyano, hydroxy, carbamoyl, carboxy, $C_{1-6}$alkanoyl and trifluoromethyl or Het$(CH_2)_m$ in which Het is a 5 or 6 membered carbocyclic ring containing one or more heteroatoms and m is 0 to 6;

$R^2$ is $C_{1-6}$alkyl, phenyl, $C_{1-6}$alkoxy, $C_{1-6}$alkylthio, hydroxy, $C_{1-6}$alkanoyl, amino, $C_{1-6}$alkylamino, di-$C_{1-6}$alkylamino, halogen, trifluoromethyl or cyano;

$R^3$ is hydrogen or $C_{1-4}$alkyl;

n is 0, 1 or 2, and the dotted line indicates the optional presence of a double bond; or a pharmaceutically acceptable salt thereof.

Preferably $R^1$ is a substituted phenyl group or benzyl group. More preferably, $R^1$ is a phenyl or benzyl group substituted by a single substituent; in particular in the 2-position. Most preferably $R^1$ is a phenyl or benzyl group substituted in the 2-position by a $C_{1-6}$alkyl group for example a methyl group.

Suitably, n is 2 and one group $R^2$ is in the 7-position. Preferably n is 0; most preferably n is 1 and the group $R^2$ is in the 7-position; more preferably n is 0.

Suitably $R^2$ is $C_{1-6}$alkylphenyl, $C_{1-6}$alkylthio, $C_{1-4}$alkanoyl, amino, $C_{1-6}$alkylamino, di$C_{1-6}$alkylamino, halogen, trifluoromethyl or cyano. Preferably $R^2$ is $C_{1-6}$alkoxy, for example methoxy.

Suitably $R^3$ is hydrogen or $C_{1-4}$alkyl; preferably hydrogen.

$C_{1-6}$alkyl groups (either alone or as part of another group) can be straight or branched.

Alkylene chains $(CH_2)_m$ in which m is 1 to 6 include straight and branched chains. For example, ethylene or α-methylmethylene

etc.

Heterocyclic groups Het, include for example, furanyl and thienyl groups; other standard groups will be apparent to those skilled in the art.

It will be appreciated that compounds of structure (I) in which one or more of $R^1$ or $R^2$ is a $C_{3-6}$alkyl group (either alone or as part of another group for example a benzyl or phenethyl group) may contain an asymmetric centre due to the presence of the $C_{3-6}$alkyl group. Such compounds will exist as two (or more) optical isomers (enantiomers/diastereoisomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

Compounds of structure (I) can form pharmaceutically acceptable acid addition salts with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as for example, citric, maleic or fumaric acids. In particular, salts formed with such carboxylic acids, especially citric acid, have improved solubility characteristics when compared to the parent compound.

In a further aspect, the present invention provides a process for the preparation of a compound of structure (I) which comprises (a) reaction of a compound of structure (II) with a compound of structure (III):

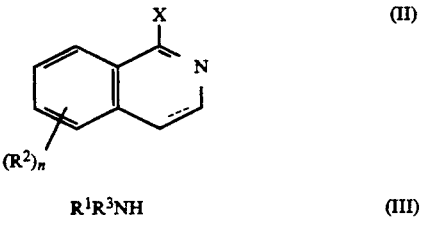

in which $R^1$, $R^2$, $R^3$ and n are as described for structure (I) and X is a group displaceable by an amine;

(b) for compounds of structure (I) in which a double bond is present and in which $R^1$ is $C_{1-6}$alkyl, $C_{3-6}$cycloalkyl, $C_{3-6}$cycloalkyl$C_{1-6}$alkyl or optionally substituted phenyl$(CH_2)_m$ or Het$(CH_2)_m$ group in which m is 1 to 6, and $R^3$ is hydrogen reaction of a compound of structure (IV) with a compound of structure (V)

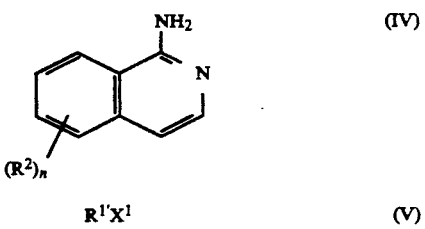

in which $R^1$, $R^2$ and n are as described for structure (I); $R^{1'}$ is $C_{1-6}$alkyl, $C_{3-6}$cycloalkyl, $C_{3-6}$cycloalkyl-$C_{1-6}$alkyl or optionally substituted phenyl$(CH_2)_m$ or Het$(CH_2)_m$ group in which m is 1 to 6 and $X^1$ is a leaving group; or (c) for compounds of structure (I) in which a double bond is present reduction of a compound of structure (VI)

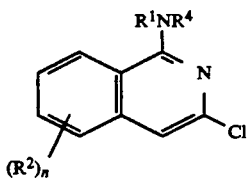

(VI)

in which $R^1$, $R^2$, and n are as described for structure (I); and $R^4$ is hydrogen or a nitrogen protecting group; and thereafter if desired,
removing any protecting groups;
converting a group $R^1$ into another group $R^1$;
forming a pharmaceutically acceptable salt.

Suitable groups X displaceable by an amine, include for example, aryl or alkylsulphonates, for example, toluene-p-sulphonate or methane sulphonate, alkylthio, alkylsulphonyl, alkylsulphinyl or alkoxy. Preferably X is a halo atom, for example, chloro or bromo, or an alkylthio group, in particular methylthio.

Suitable leaving groups $X^1$ will be apparent to those skilled in the art and include for example a halo moiety, preferably chloro or bromo.

Suitable nitrogen protecting groups $R^4$ will be apparent to those skilled in the art for example as described in "Protective Groups in Organic Synthesis" T. W. Greene, 1981 (Wiley).

The reaction between compounds of structure (II) and compounds of structure (III) is carried out at elevated temperature optionally in the presence of an organic solvent. Suitable solvents include, for example, dimethylformamide, tetrahydrofuran, dioxan, ethanol or anisole. Preferably the reaction is carried out at elevated temperature under fusion conditions in the absence of a solvent.

The reaction between compounds of structure (IV) and compounds of structure (V) is carried out in an organic solvent at a temperature of between ambient and reflux temperature of the solvent used, preferably in the presence of a base. Suitable solvents include for example, lower alkanols such as ethanol. Suitable bases include for example, tertiary amine bases such as triethylamine.

The reduction of a compound of structure (VI) is carried out by for example hydrogenation, over a noble metal catalyst in a suitable solvent. Suitably the reaction is carried out over a palladium on carbon catalyst in ethanol as a solvent.

The intermediates of structure (II) and (IV) can be prepared by standard techniques.

The intermediates of structure (III) and (V) are commercially available or can be prepared by standard techniques.

The compounds of structure (I) and their pharmaceutically acceptable salts exert an anti-secretory effect by inhibition of the gastrointestinal $H^+K^+ATPase$ enzyme.

In further aspect therefore the present invention provides compounds of structure (I) and pharmaceutically acceptable salts thereof for use in therapy. The compounds of structure (I) and their pharmaceutically acceptable salts inhibit exogenously and endogenously stimulated gastric acid secretion and are useful in the treatment of gastrointestinal diseases in mammals, in particular humans. Such diseases include, for example, gastric and duodenal ulcers, aspiration pneumonitis and Zollinger-Ellison Syndrome.

Further, the compounds of structure (I) can be used in the treatment of other disorders where an anti-secretory effect is desirable for example in patients with gastritis, NSAID induced gastritis, acute upper intestinal bleeding, in patients with a history of chronic and excessive alcohol consumption, and in patients with gastro oesophageal reflux disease (GERD).

In addition to the foregoing use the compounds of structure (I) can be expected to be of use in medicine as inhibitors of bone resorption. In normal subjects there is a balance between bone resorption and bone formation, however in subjects with bone affected diseases such as osteoporosis, Paget's disease and hyperparathyroidism and related disorders this balance is disturbed. As a consequence the subject suffers a loss of bone tissue, decreased bone mass and bone fragility which can result in fracturing of bones. Bone resorption (or bone loss) is associated with the activity of osteoclast cells, and it is thought that agents which inhibit the activity of such cells (and so inhibit bone resorption) will have a beneficial effect on the reduction of bone loss and be of benefit in the treatment of the above-noted disease states. The present compounds can be expected to be inhibitors of osteoclast activity an bone resorption and to be of use in medicine in the treatment of diseases in which bone loss is a factor, in particular osteoporosis, Paget's disease and hyperparathyroidism.

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The present invention therefore provides a method of inhibiting gastric acid secretion which comprises administering to a mammal in need thereof an effective amount of a compound of the formula (I) or a pharmaceutically acceptable salt thereof; and a method of treatment of diseases of the stomach or intestine based on increased acid secretion which comprises administering to a mammal in need thereof an effective amount of a compound of the formula (I) or a pharmaceutically acceptable salt thereof; and a method of inhibiting bone resorption which comprises administering to a subject in need thereof an effective amount of a compound of structure (I) or a pharmaceutically acceptable salt thereof.

When used in therapy, for the treatment of gastrointestinal diseases and other conditions caused or exacerbated by gastric acidity, the daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more. In addition, the compounds of tee present invention can be co-administered with further active ingredients, such as antacids (for example magnesium carbonate or hydroxide and aluminium hydroxide), non-steroidal antiinflammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl $PGE_2$, or histamine $H_2$-antagonists (for example, cimetidine).

The following examples illustrate the invention. Temperatures are recorded in degrees centigrade.

EXAMPLE 1

1-[(2-Methylphenyl)amino]isoquinoline hydrochloride

1-Chloroisoquinoline (J. O. C. (1958), 23, 1071) (1.64 g, 0.01 mol) and o-toluidine (1.07 g, 0.01 mol) were heated together at reflux temperature in dry dioxan (20 ml) for 18 hours. After this time a light brown oil had precipitated in the hot solution. After cooling the mixture was evaporated to dryness to give an off-white, sticky solid. This was treated with diethyl ether (50 ml), collected, washed with ether and dried to give a white solid (2.07 g). This solid was crystallised from ethanol/ether to give the title compound (1.97 g) as its hydrochloride salt, m.p. 229°–231°.

$C_{16}H_{14}N_2 \cdot HCl$:
Found: C 71.4, H 5.7, N 10.4, Cl⁻ 13.0%;
Requires: C 71.0, H 5.6, N 10.4, Cl⁻ 13 1%;

EXAMPLE 2

1-(Benzylamino)isoquinoline

1-Chloroisoquinoline (1.64 g, 0.01 mol) and benzylamine (2.14 g, 0.02 mol) were mixed at room temperature and heated, with stirring, in an oil-bath at 50° for 4 hours. The mixture was cooled to give a crystalline solid which was equilibrated between methylene chloride ($CH_2Cl_2$) and aqueous $Na_2CO_3$. The $CH_2Cl_2$ fraction was washed with water, dried and evaporated to dryness to give an oil which crystallised on standing (3.0 g). This material was twice re-crystallised from ether/40–60 petroleum ether to give the title compound as buff crystals, m.p. 101°–102°.

$C_{16}H_{14}N_2$:
Found: C 82.0, H 6.1, N 12.1%;
Requires: C 82.0, H 6.0, N 12.0%;

EXAMPLE 3

1-[(2-Methylphenylmethyl)amino]isoquinoline hydrochloride

Substituting 2-methylbenzylamine (2.03 gm, 0.017 mol) for benzylamine and using corresponding molar proportions of the other reagents in Example 2 gave a brown oil (3.1 g). This was dissolved in the minimum amount of methanol and 2N HCl added to precipitate a buff-coloured solid which was collected, washed with water and dried (1.67 g).

Crystallisation from absolute ethanol gave the title compound as its hydrochloride salt, m.p. 244°–248°.

$C_{17}H_{16}N_2 \cdot HCl$:
Found: C 71.6 H 6.0, N 9.8, Cl⁻ 12.3%;
Requires: C 71.7, H 6.0, N 9.8, Cl⁻ 12.5%;

EXAMPLE 4

1-[(2-Methoxyphenylmethyl)amino]isoquinoline

Substituting 2-methoxybenzylamine (1.67 g 0.0122 mol) for benzylamine and using corresponding molar proportions of the other reagents in Example 2 gave a brown oil which was dissolved in the minimum amount of methanol and aqueous 2NHCl added. The solution was basified with 2N. NaOH and the precipitated buff-coloured solid collected, washed with water and dried (1.60 g). This material was crystallised from methanol to give the title compound (1.0 g) as buff-coloured needles, m.p. 111°–113°.

$C_{17}H_{16}N_2O$:
Found: C 77.2, H 6.1, N 10.5%;
Requires: C 77.2, H 6.1, N 10.6%:

EXAMPLE 5

1-[N-Methylphenylmethylamino]isoquinoline

Substituting N-methylbenzylamine (1.48 g, 0.0122 mol) for benzylamine and using corresponding molar proportions of the other reagents in Example 2 gave a brown oil (2.42 g, may contain trace of $CH_2Cl_2$). This material was purified by column chromatography on silica gel using $CH_2Cl_2$ as eluting solvent to give a pale-green oil (0.82 g) which solidified on standing and was re-crystallised from ether/40–60 petroleum ether to give the title compound (0.76 g), m.p. 53.5°–54.5°.

$C_{17}H_{16}N_2$:
Found: C 82.1, H 6.4, N 11.2%;
Requires: C 82.2, H 6.5, N 11.3%;

EXAMPLE 6

1-(2-Phenylethylamino)isoquinoline.

Substituting 2-phenylethylamine (1.48 g 0.0122 mol) for benzylamine and using corresponding molar proportions of the other reagents in Example 2 gave a brown oil which crystallised on standing (2.48 g). This material was crystallised twice from ether/40–60 petroleum ether to give the title compound (1.03 g) as a white solid, m.p. 110°–112°.

$C_{17}H_{16}N_2$:
Found: C 82.4, H 6.7, N 11.2%;
Requires: C 82.2, H 6.5, N 11.3%;

EXAMPLE 7

(R)-(−)-1-[(α-Methylphenylmethyl)amino]isoquinoline

Substituting R-(+)-α-methylbenzylamine (1.48 g, 0.0122 mol) for benzylamine and using corresponding molar proportions of the other reagents in Example 2 gave a brown oil which could not be crystallised. This material was chromatographed on silica gel using methylene chloride as eluting solvent. Fractions were monitored by thinlayer chromatography and those containing product were combined and evaporated to dryness to give an oil (0.6 g) which solidified on standing. Crystallisation from ether/40–60 petroleum ether gave the title compound (0.36 g) as pale-yellow crystals, m.p. 79°–80°, $[\alpha]_D = 25° -204.6$.

$C_{17}H_{16}N_2$:
Found: C 82.0, H 6.5, N 11.3%;
Requires: C 82.2, H 6.5, N 11.3%;

EXAMPLE 8

(S)-(+)-1-[(α-Methylphenylmethyl)amino]isoquinoline

Substituting S-(−)-α-methylbenzylamine (1.48 g 0.0122 mol) for R-(+)-α-methylbenzylanine and using corresponding molar proportions of the other reagents in Example 7 gave, after chromatography a crystalline solid (0.79 g). This material was re-crystallised from ether/40–60 petroleum ether to give the title compound (0.37 g), m.p. 81°–83°, $[\alpha]_D = 25° +205.7$.

$C_{17}H_{16}N_2$:
Found: C 82.1, H 6.5, N 11.3%;
Requires: C 82.2, H 6.5, N 11.3%;

EXAMPLE 9

1-[(4-Methoxyphenylmethyl)amino]isoquinoline

Substituting 4-methoxybenzylamine (3.34 g, 0.0244 mol) for benzylamine and using corresponding molar proportions of the other reagents in Example 2 gave a green oil which could not be crystallised. This material was chromatographed on silica gel using $CH_2Cl_2$ as eluting solvent. Fractions containing product were combined and evaporated to dryness to give a green oil (1.6 g). This was crystallised from ether/40–60 petroleum ether to give the title compound (1.07 g) as a colourless crystalline solid, m.p. 55°–56°.

$C_{17}H_{16}N_2O$:
Found: C 77.4, H 6.0, N 10.6%;
Requires: C 77.3, H 6.1, N 10.6%;

EXAMPLE 10

1-[(2-Thienylmethyl)amino]isoquinoline

Substituting 2-thiophenemethylamine (1.39 g, 0.0122 mol) for benzylamine and using corresponding molar proportions of the other reagents in Example 2 gave a brown oil which solidified on scratching (1.25 g). This material could not be satisfactorily crystallised so it was chromatographed on silica gel using $CH_2Cl_2$ as eluent. Fractions containing major product (t.l.c.) were combined and evaporated to dryness to give an oil which solidified on standing (0.9 g). This material was crystallised twice from ether/40–60 petroleum ether to give the title compound (0.6 g) as orange-yellow crystals, m.p. 86.5°–87.5°.

$C_{14}H_{12}N_2S$:
Found: C 70.5, H 5.0, N 11.7%;
Requires: C 70.0, H 5.0, N 11.7%;

EXAMPLE 11

1-[(2-Furylmethyl)amino]isoquinoline

Substituting furfurylamine (1.2 g, 0.0122 mol) for 2-thiophenemethylamine and using corresponding molar proportions of the other reagents in Example 10 gave, after similar chromatography, a pale-orange oil which solidified on scratching (1.14 g). This material was crystallised twice from ether/40–60 petroleum ether to give the title compound (0.76 g) as pale-pink crystals, m.p. 76°–77°.

$C_{14}H_{12}N_2O$:
Found: C 75.1, H 5.3, N 12.5%;
Requires: C 75.0, H 5.4, N 12.5%;

EXAMPLE 12

5-Methoxy-1-[(benzylmethyl)amino]isoquinoline hydrochloride

5-Methoxy-1-chloroisoquinoline (J.A.C.S. (1947), 69, 1939) (1.5 g, 0.00777 mol) and benzylamine (1.67 g, 0.0156 mol) were mixed at room temperature and heated, with stirring, in an oil-bath at 150° for 4 hours. After cooling the mixture was equilibrated between $CH_2Cl_2$ and aqueous $Na_2CO_3$. The $CH_2Cl_2$ fraction was washed with water, dried and evaporated to dryness. The oil produced was dissolved in the minimum amount of methanol and aqueous 2N. HCl added to precipitate a buff solid which was collected, washed with water and dried (2.15 g). This material was crystallised from ethanol/methanol to give the title compound (1.40 g) as its hydrochloride salt, m.p. 247°–252° (Dec).

$C_{17}H_{16}N_2O \cdot HCl$:
Found: C 67.9, H 5.7, N 9.3, Cl⁻ 11.9%;
Requires: C 67.9, H 5.7, N 9.3, Cl⁻ 11.8%;

EXAMPLE 13

5-Methoxy-1-[(2-methylphenyl)amino]isoquinoline

5-Methoxy-1-chloroisoquinoline (1.5 g, 0.00777 mol) and o-toluidine (0.835 gm, 0.00777 mol) were mixed in anisole (10 ml) and heated with stirring in an oil-bath at 140° for four hours. After cooling the mixture was dissolved in methanol and ether was added to precipitate a tacky solid. The solvent was decanted off and the precipitate washed with more ether. The insoluble residue was equilibrated between N. HCl and ether, the aqueous acid solution filtered and basified with saturated aqueous $Na_2CO_3$ to precipitate a buff solid which was collected, washed with water and dried (0.77 g). This material was crystallised from diethyl ether to give the title compound (0.62 g) as fluffy, light-buff needles, m.p. 111°–112°.

$C_{17}H_{16}N_2O \cdot 0.15 \, Et_2O$:
Found: C 76.5, H 6.4, N 10.2%;
Requires: C 76.7, H 6.4, N 10.2%;

EXAMPLES 14

5-Methoxy-1-[(2-methylphenylmethyl)amino]isoquinoline

Substituting 2-methylbenzylamine (1.25 g, 0.01033 mol) for benzylamine and using corresponding molar proportions of the other reagents in Example 12 produced, after equilibration between aqueous $Na_2CO_3$ and $CH_2Cl_2$ and drying and evaporation of the organic phase a light brown solid (1.09 g). This material was crystallised from ethanol/$H_2O$ to give the title compound (0.7 g) as its partial hydrate, m.p. 121°–125° (Not sharp).

$C_{18}H_{18}N_2O.0.2H_2O$:
Found: C 76.8, H 6.6, N 9.9%;
Requires: C 76.8, H 6.6, N 10.0%;

EXAMPLE 15

1-[(2-Methoxyphenylmethyl)amino]-6,7-dimethoxyisoquinoline hydrochloride 6,7-Dimethoxy-1-chloroisoquinoline (J. Am. Pharm. Assoc., Sci. Ed. (1952), 41, 643–50; C.A. 47, 11205d.) (1.0 gm, 0.00447 mol) and 2-methoxybenzylamine (1.22 gm, 0.00894 mol) were mixed at room temperature and heated, with stirring, in an oil-bath at 140° for 1.5 hours. After cooling the mixture was dissolved in chloroform and the solution washed with saturated $NaHCO_3$ solution and water, dried and evaporated. The resulting oil was chromatographed on silica gel, using chloroform as eluent. Fractions were monitored by t.l.c. and those containing pure product were combined, evaporated to dryness and the residue (0.25 g) dissolved in ethanol containing ethanolic hydrogen chloride. This solution was evaporated to dryness and the residue crystallised from ethanol/diethyl ether to give the title compound as its hydrochloride salt (0.22 gm), m.p. 225°–229°.

$C_{19}H_{20}N_2O_3.HCl.0.25H_2O$:
Found: C 62.3, H 5.8, N 7.5, $Cl^-$ 9.8%;
Requires: C 62.5, H 5.9, N 7.7, $Cl^-$ 9.7%;

EXAMPLE 16

1-[(2-Methylphenyl)amino]-6,7-dimethoxyisoquinoline hydrochloride

Substituting o-toluidine (1.91 g, 0.0178 mol) for 2-methoxybenzylamine and using corresponding molar proportions of other reagents in Example 15 produced, after column chromatography, an oil (0.54 gm). This was dissolved in ethanolic hydrogen chloride, the solution evaporated to dryness and the residue crystallised from ethanol/diethyl ether to give the title compound as its hydrochloride salt (0.40 g), m.p. 253°–255°.

$C_{18}H_{18}N_2O_2.HCl.0.2 H_2O$:
Found: C 64.4, H 5.8, N 8.1, $Cl^-$ 10.3%;
Requires: C 64.6, H 5.8, N 8.4, $Cl^-$ 10.6%;

EXAMPLE 17

1-[(2-Methoxyphenylmethyl)amino]-6-methoxyisoquinoline hydrochloride.

6-Methoxy-1-chloroisoquinoline (JACS. (1947), 69, 1939) (1.65 g, 0.0085 mol) and 2-methoxybenzylamine (2.33 g, 0.017 mol) were mixed at room temperature and stirred in an oil-bath at 140° for 2 hours. After cooling the solid mass was dissolved in chloroform and the solution washed with saturated $NaHCO_3$ (x3) and water, dried and evaporated to give a pale-orange oil (2.3 g). This was dissolved in ethanol, ethanolic hydrogen chloride added and the solution evaporated to dryness. The residual solid was crystallised from ethanol/diethyl ether to give the title compound as its hydrochloride salt (1.24 g), m.p. 222°–227°.

$C_{18}H_{18}N_2O_2.HCl.0.25H_2O$:
Found: C 64.3, H 5.7, N 8.2, $Cl^{31}$ 10.5%;
Requires: C 64.5, H 5.9, N 8.3, $Cl^-$ 10 6%;

EXAMPLE 18

1-[(2-Methylphenyl)amino]-6-methoxyisoquinoline hydrochloride

Substituting o-toluidine (1.37 g, 0.0128 mol) for 2-methoxybenzylamine and using corresponding molar proportions of other reagents in Example 17 gave, after equilibration of the product between aqueous $NaHCO_3$ and $CHCl_3$ a dark-orange oil (1.6 g). This was chromatographed on silica gel using chloroform as eluent to give a pale-yellow oil (0.5 g). This was dissolved in ethanolic hydrogen chloride, the solution evaporated to dryness and the residue crystallised from ethanol/diethyl ether to give the title compound as its hydrochloride salt (0.4 g), m.p. 230°–240°.

$C_{17}H_{16}N_2O.HCl.0.1H_2O$:
Found: C 67.3, H 5.6, N 9.2, $Cl^-$ 11.4%;
Requires: C 67.5, H 5.7, N 9.3, $Cl^-$ 11.7%;

EXAMPLE 19

1-[(2-Methoxyphenylmethyl)amino]-7-methoxyisoquinoline hydrochloride

7-Methoxy-1-chloroisoquinoline (JACS, (1947), 69, 1939) (1.5 g, 0.00775 mol) and 2-methoxybenzylamine (2.12 g, 0.015 mol) were mixed at room temperature and heated with stirring in an oil-bath at 140° for 2 hours. After cooling the solidified mass was equilibrated between chloroform and saturated aqueous $NaHCO_3$. The chloroform solution was washed with water, dried and evaporated to dryness to produce an oil which was chromatographed on silica gel using chloroform as eluent. Monitoring fractions by t.l.c. and H.P.L.C. and combination of appropriate samples gave, after evaporation, a buff-coloured oil (0.58 g). This was dissolved in ethanolic hydrogen chloride, the solution evaporated to dryness and the residue crystallised from ethanol/ether to give a buff solid (0.54 g). This was re-crystallised from ethanol/ether, with charcoaling, to give the title compound as its white hydrochloride salt (0.35 g), m.p. 197°–210°.

$C_{18}H_{18}N_2O_2.HCl.0.5H_2O$:
Found: C 63.3, H 6.0, N 8.1, $Cl^-$ 10.6%;
Requires: C 63.6, H 5.9, N 8.2, $Cl^-$ 10.4%;

EXAMPLE 20

1-[(2-Methylphenyl)amino]-7-methoxyisoquinoline hydrochloride

Substituting o-toluidine (1.01 g, 0.0095 mol) for 2-methoxybenzylamine and using corresponding molar proportions of other reagents in Example 19 gave, after column chromatography (silica gel, $CHCl_3$ eluent) a pale-yellow oil (0.6 g). This oil was dissolved in ethanol, ethanolic hydrogen chloride added and the solution evaporated to dryness. The solid produced was crystallised from ethanol/diethyl ether to give the title compound as its hydrochloride salt (0.4 g), m.p. 150°–152°.

$C_{17}H_{16}N_2O.HCl. H_2O$:
Found: C 64.0, H 5.6, N 8.8, $Cl^-$ 11.1%
Requires: C 64.0, H 6.0, N 8.8, $Cl^-$ 11.1%

EXAMPLE 21

1-Benzylamino-3,4-dihydroisoquinoline hydrochloride.

1-Methylthio-3,4-dihydroisoquinoline hydroiodide (J. Het. Chem. (1979), 16, 1313-1316) (0.9 g, 0.00295 mol), benzylamine (0.32 g, 0.00299 mol) and dry dimethylformamide (10 ml) were mixed at room temperature and heated with stirring in an oil-bath for 1 hour at 110°. The mixture was cooled and poured onto water (100 ml) to give a clear solution (pH=8). This solution was basified with 2N. NaOH (pH=11), and extracted with ethyl acetate (x 2). The ethyl acetate solution was washed with water, dried and evaporated to give a colourless oil. This material was dissolved in ethanol/ether and anhydrous ethanolic HCl added. On standing in the cold a white solid crystallised and was collected (0.9 g). This material was re-crystallised twice from ethanol/ether to give the title compound (0.53 g) as its slightly green hydrochloride salt, m.p. 229°–232°.

$C_{16}H_{16}N_2.HCl$: 
Found: C 70.5, H 6.2, N 10.2, Cl− 13.2%;
Requires: C 70.5, H 6.3, N 10.3, Cl− 13.0%;

EXAMPLE 22

1-[(2-Methylphenylmethyl)amino]-3,4-dihydroisoquinoline hydroiodide.

1-Methylthio-3,4-dihydroisoquinoline hydroiodide (1.52 g, 0.005 mol) was dissolved in a solution of ethanol (50 ml) containing 2-methylbenzylamine (0.61 g, 0.005 mol). The colourless solution was heated at reflux temperature for six hours with effluent gases being passed through a CHLOROS trap. The solution was then cooled and stood in the refrigerator overnight to give white crystals (1.38 g). This material was crystallised from methanol/ ethanol to give the title compound (1.06 g) as its hydroiodide salt, m.p. 241°–243°.

$C_{17}H_{18}N_2. HI$: 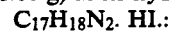
Found: C 53.8, H 5.0, N 7.4, I− 34.3%;
Requires: C 54.0, H 5.1, N 7.4, I− 33.6%;

EXAMPLE 23

1-[(4-Hydroxyphenylmethyl)amino]-3,4-dihydroisoquinoline

1-Methylthio-3,4-dihydroisoquinoline hydroiodide (0.6 g, 0.00197 mol) and 4-hydroxybenzylamine (0.24 g, 0.00195 mol) were heated together at reflux temperature in ethanol (25 ml) for five hours. Effluent gases were passed through a CHLOROS trap. The mixture was then cooled and the ethanol evaporated off at reduced pressure. The tacky residue was dissolved in dilute HCl and the solution extracted with ethyl acetate. The clear aqueous solution was basified with 6N. NaOH and re-extracted with ethyl acetate. The latter organic extract was washed with water, dried and evaporated to dryness to give a white sticky solid. This was treated with ether and the ether decanted off. The residual solid was crystallised from absolute ethanol to give the title compound (0.11 g) as white crystals, m.p. 177°–179°.

$C_{16}H_{16}N_2O.0.1\ H_2O$: 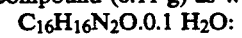
Found: C 75.2, H 6.5, N 10.8%;
Requires: C 75.6, H 6.4, N 11.0%;

EXAMPLE A

A table for oral administration is prepared by combining

|  | Mg/Tablet |
| --- | --- |
| Compound of structure (I) | 100 |
| lactose | 153 |
| Starch | 33 |
| crospovidone | 12 |
| microcrystalline cellulose | 30 |
| magnesium stearate | 2 |
|  | 330 mg | into a 9 mm tablet.

EXAMPLE B

An injection for parenteral administration was prepared from the following

|  | % w:w |
| --- | --- |
| Compound of structure 1 | 0,50% (w:v) |
| 1M citric acid | 30% (v:v) |
| sodium hydroxide (qs) | to pH 3.2 |
| water for injection EP | to 100 ml |

The compound of structure 1 was dissolved in the citric acid and the pH slowly adjusted to pH 3.2 with the sodium hydroxide solution. The solution was then made up to 100 ml with water, sterilised by filtration and sealed into appropriately size ampoules and vials.

Biological Data (A) H+K+ATPase Activity.

The effects of a single high concentration (100 μM) of a compound of structure (I) on K-stimulated ATPase activity in lyophilised gastric vesicles was determined. Preferred compounds of structure (I) were also tested over a range of concentrations to determine IC$_{50}$ values.

(i) Preparation of lyophilised pastric vesicles (H/K-ATPase).

Lyophilised gastric vesicles were prepared from pig fundic mucosa after the method of Keeling et. al. (Biochem. Pharmacol., 34, 2967, 1985).

(ii) K+-stimulated ATPase activity.

K+-stimulated ATPase activity was determined at 37° in the presence of the following: 10 mM Pipes/Tris buffer pH 7.0, 2 mM MgSO$_4$, 1 mM KCl, 2 mM Na$_2$ATP and 3–6 μg protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulphoxide which up to the highest concentration used had no effect on K+-stimulated ATPase activity.

The effect of the highest concentration of each compound of structure (I) on the recovery of a standard amount of inorganic phosphate was also determined.

(iii) Results.

The compounds of examples 1 to 4 and 6 to 23 gave IC$_{50}$ values in the range of from 0.48 to 60 μM.

What is claimed is:

1. A compound of structure (I)

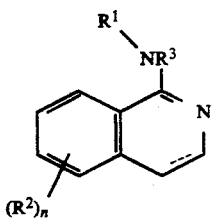

in which:
- $R^1$ is $C_{3-6}$cycloalkyl, $C_{3-6}$cycloalkyclC$_{1-6}$alkyl, phenyl $(CH_2)_m$ the phenyl group being optionally substituted by 1-3 radicals selected from $C_{1-6}$alkyl, $C_{1-6}$alkoxy, amino-$C_{1-6}$alkylthio, halogen, cyano, hydroxy, carbamoyl, carboxy, $C_{1-6}$alkanoyl and trifluoromethyl or Het $(CH_2)_m$ in which Het is furyl or thienyl and m is 0 to 6;
- $R^2$ is $C_{1-6}$alkyl, phenyl, $C_{1-6}$alkoxy, $C_{1-6}$alkylthio, hydroxy, $C_{1-6}$alkanoyl, amino, $C_{1-6}$alkylamino, di-$C_{1-6}$alkyl-amino, halogen, trifluoromethyl or cyano;
- $R^3$ is hydrogen or $C_{1-4}$alkyl;
- n is 0 or 1 and the dotted line indicates the optional presence of a double bond; provided that i) when n is 0, and there is no optional double bond; $R^1$ is not phenyl, cyclopropyl, cyclopentyl, 2-fluorophenyl phenylethyl or benzyl; (ii) when $R^2$ is chloro and there is no optional double bond, $R^1$ is not cyclopropyl; iii when $R^2$ is alkyl, hydroxy or alkoxy, n is 1 and the optional double bond is present, then $R^1$ is not phenyl $(CH_2)_m$ in which m is 0 to 3 and the phenyl is optionally substituted by halogen, alkoxy or alkyl; or a pharmaceutically acceptable salt thereof.

2. A compound according to claim 1 in which $R^1$ is a substituted benzyl group.

3. A compound according to claim 1 in which $R^1$ is a phenyl or benzyl group substituted by a single substituent.

4. A compound according to claim 3 in which $R^1$ is a phenyl or benzyl group substituted by a single substituent in the 2-position.

5. A compound according to claim 4 in which the substituent is a $C_{1-6}$alkyl group.

6. A compound according to claim 5 which is 1-[(2-Methoxyphenylmethyl)amino]isoquinoline hydrochloride or 1-[(2-Methylphenyl)amino]-7-methoxyisoquinoline hydrochloride.

7. A pharmaceutical composition comprising a compound according to any one of claims 1 to 6 and a pharmaceutically acceptable carrier.

8. A method of inhibiting gastric acid secretion which comprises administering to a mammal in need thereof, an effective amount of a compound of structure (I) as described in claim 1.

9. A method of treatment of gastrointestinal diseases, and other conditions caused or exacerbated by gastric acidity which comprises administering to a mammal in need thereof an effective amount of a compound of structure (I) in as claimed in claim 1.

* * * * *

UNITED STATES PATENT AND TRADEMARK OFFICE
CERTIFICATE OF CORRECTION

PATENT NO. : 5,200,417
DATED : April 6, 1993
INVENTOR(S) : Thomas H. Brown, et al.

It is certified that error appears in the above-identified patent and that said Letters Patent is hereby corrected as shown below:

Column 13, line 12, replace "$C_{3-6}$cycloalkycl" with --$C_{3-6}$cycloalkyl--.

Column 13, line 21, replace "di-$C_{1-6}$alkyl-amino" with --di-$C_{1-6}$alkylamino--.

Signed and Sealed this

Seventh Day of June, 1994

Attest:

BRUCE LEHMAN

Attesting Officer     Commissioner of Patents and Trademarks